United States Patent [19]

Pillai et al.

[11] Patent Number: 5,582,832
[45] Date of Patent: Dec. 10, 1996

[54] COMPOSITIONS FOR TOPICAL APPLICATION TO SKIN

[75] Inventors: Sreekumar Pillai, Wayne; Manisha N. Mahajan, Edgewater; Anthony V. Rawlings, Wyckoff, all of N.J.

[73] Assignee: Chesebrough-Pond's USA Co., Division of Conopco, Inc., Greenwich, Conn.

[21] Appl. No.: 469,454

[22] Filed: Jun. 6, 1995

[51] Int. Cl.$^6$ .................................................. A61K 7/48
[52] U.S. Cl. ................ 424/401; 424/70.1; 424/78.03; 424/61; 424/404
[58] Field of Search ................ 424/401, 404, 424/59, 78.03, 60, 70.1; 514/847, 937, 938

[56] References Cited

U.S. PATENT DOCUMENTS 4,626,529  12/1986  Grollier ................................ 514/159
5,206,020  4/1993  Critchley et al. .................... 424/401

FOREIGN PATENT DOCUMENTS 2101101  2/1994  Canada.

*Primary Examiner*—Thurman K. Page
*Assistant Examiner*—Sharon Howard
*Attorney, Agent, or Firm*—Rimma Mitelman

[57]  ABSTRACT

Compositions for treating skin which contain azole in combination with a lipid ingredient. The compositions attain keratinocyte differentiation and provide additional benefits. Also disclosed is a method of improving or preventing the appearance of wrinkled, flaky, aged, photodamaged skin by applying to skin a composition containing in a cosmetically acceptable vehicle an azole and a lipid ingredient.

6 Claims, No Drawings

COMPOSITIONS FOR TOPICAL APPLICATION TO SKIN

FIELD OF THE INVENTION

The invention relates to compositions for topical application to human skin which compositions contain an azole and a lipid component and to methods of using the compositions for treatment and conditioning of skin.

BACKGROUND OF THE INVENTION

The top layer of human skin or the epidermis is composed of many different cell types including keratinocytes, melanocytes and langerhans cells. Keratinocytes are the major cell type of the epidermis (75–80% of the total number of cells in the human epidermis). Within the epidermis the keratinocytes reside in four distinct stages of differentiation. The basal layer rests on the basal lamina separating epidermis from the dermis. These cells are large columnar rapidly proliferating cells. These basal cells migrate upward within the epidermis, initiated by the process of differentiation. The layer above the basal cells is the spinous layer. The cells in the spinous layer initiate the production of proteins characteristic of the differentiated epidermis. The granular layer, lying above the spinous layer, is characterized by electron-dense granules. This layer is responsible for the synthesis of lipid molecules required for the formation of the water impermeable barrier of the skin. The topmost layer of the skin, the stratum corneum, is formed from the granular layer by the destruction of cellular organelles. The cells in the stratum corneum, corneocytes, contain extensively cross-linked proteins, surrounded by a highly resistant cell envelope. The corneocytes are embedded in a bed of specific lipid structures (analogous to bricks on a bed of mortar) and this structure provides the protective barrier for the skin. The outermost layer of corneocytes is peeled off from the skin during the normal process of desquamation. Differentiation of the epidermal keratinocytes is the driving force for the normal desquamation process to occur. Epidermal differentiation is important for providing the essential function of the skin, namely to provide a protective barrier against the outside environment and to prevent loss of water from the body. The basal cells which have the highest rate of growth, are the least differentiated. The most differentiated cells of the stratum corneum do not have the ability to grow.

Initiation of differentiation of keratinocytes is accompanied by inhibition of their growth. The rate of synthesis of DNA determined by the incorporation of radiolabeled substrate [$^3$H] thymidine, is an indicator of the rate of growth of the cells. A decrease in DNA synthesis therefore indicates decrease in growth and increase in differentiation of keratinocytes.

The present invention is based, in part, on the discovery that a combination of specific active ingredients, namely an azole and short chain lipids, results in synergistic increase in differentiation, which in turn results in increased benefits to skin, such as improved conditioning, improved youthful appearance, decrease in wrinkle appearance, moisturizing, and treatment of photodamaged skin and various skin disorders, such as acne, xerosis, ichthyosis and psoriasis.

1,25-$(OH)_2D_3$ is the major biologically active metabolite of vitamin $D_3$. 1,25-$(OH)_2D_3$ plays a central role in regulating blood calcium levels by increasing bone resorption and calcium absorption from intestine. Recent studies indicate that exogenous or endogenous 1,25-$(OH)_2D_3$ and its precursor 25-hydroxyvitamin D (25D) inhibit DNA synthesis (i.e., inhibit growth) and induce differentiation of keratinocytes. See e.g., Pillai et al. "1,25-Dihydroxy vitamin D Production and Receptor Binding in Human Keratinocytes Varies with Differentiation" *The Journal of Biological Chemistry*, Vol. 263, No. 11, (Apr. 15, 1988), pp. 5390–95; and Hashimoto et al., "Growth-inhibitory effects of 1,25-Dihydroxy vitamin $D_3$ on Normal and Psoriatic Keratinocytes" *British Journal of Dermatology* (1990) Vol. 123, pp. 93–98.

Unfortunately, exogenously supplied (from blood and topically applied) as well as endogenously synthesized 1,25D is rapidly inactivated in epidermal cells (keratinocytes) by further hydroxylations. Inactivation of 1,25D is achieved in cells by further hydroxylations of 1,25D, beginning at positions C24 followed by C23. The present invention describes a method to inhibit this inactivation of 1,25D and thus potentiate the action of 1,25D on keratinocyte cell maturation. Inhibition of 1,25D degradation by imidazoles and potentiation of its action has been described in other cell systems; Avery S. H. et al., "Inhibition of the Hypercalcemic Action of Vitamin D with Imidazole", *Endocrinology*, 1971, Vol. 89, pp. 951–957; Reinhart T. A. et al., "Ketoconazole Inhibits Self-induced Metabolism of 1,25-Dihydroxyvitamin D and Amplifies Vitamin D Receptor Upregulation in Rat Osteosarcoma Cells", *Arch Biochem Biophys.*, 1989, Vol. 272, pp. 459–465. However, the art does not teach use of azoles in combination with ceramides to enhance the maturation benefits of 1,25D in keratinocytes or in any other cell systems.

All the vitamin D hydroxylases, including the 25 and 1 hydroxylase which activate the vitamin D to the active 1,25D and the 24 and 23 hydroxylases which inactivate the 1,25D belong to a class of monooxygenases requiring a heme containing cytochrome P450 component as part of the multienzyme complex. A class of antimicotic agents containing an imidazole molecule substituted with aromatic side chains (known as "azoles") are potent inhibitors of cytochrome P450 dependent enzymes. These azoles have a wide variety of actions including inhibition of P450 enzyme systems involved in vitamin D metabolism; Avery, S. H. et al., "Inhibition of the Hypercalcemic Action of Vitamin D With Imidazole", *Endocrinology*, 1971, Vol. 89, pp. 951–957. The effect of imidazoles on inhibition of vitamin D hydroxylation has been therapeutically used in the control of hypervitaminosis D; (Glass, A. R. et al., "Ketoconazole Reduces Elevated Serum Levels of 1,25-Dihydroxyvitamin D in Hypercalcemic Sarcoidosis", *J. Endocrinol. Invest.*, Vol. 13, (1990), pp. 407–413); regulation of blood calcium; (Avery, S. H. et al., "Inhibition of the Hypercalcemic Action of Vitamin D With Imidazole", *Endocrinology*, 1971, Vol. 89, pp. 951–957); and in enhancing the action of 1,25D; (Reinhart, T. A. et al., "Ketoconazole Inhibits Self-induced Metabolism of 1,25-Dihydroxyvitamin D and Amplifies Vitamin D Receptor Upregulation in Rat Osteosarcoma Cells", *Arch Biochem Biophys.*, Vol. 272, (1989), pp. 459–465). Most of these studies used ketoconazole (an azole), an established inhibitor of vitamin D metabolism.

Application of azoles in skin related area is restricted to its action as an antimicrobial agent. See, Gupta, A. K. et al. "Antifungal Agents: An Overview Part I and II", *J. Am. Acad. Derm.*, Vol. 30, (1994) pp. 677–698 and 911–933). Ketoconazole is also used commercially in shampoos for dandruff control. Recent studies also suggest the therapeutic value of azoles in inflammatory skin diseases, such as seborrheic dermatitis; Taieb, A. et al., "Topical Ketoconazole for Infantile Seborrhoeic Dermatitis", *Dermatologica*, Vol. 181, (1990), pp. 26–32; Faergemann, J., "Treatment of Seborrhoeic Dermatitis of the Scalp With Ketoconazole Shampoo", *Acta Derm. Venerol.* (Stockh) Vol. 70, (1990), pp. 171–172. Bifonazole has been shown to exert direct anti-inflammatory activity in histamine induced erythema; Petri, H. et al., "Investigations Into The Anti-inflammatory Effect of Bifonazole", In: Hay R. J. (ed). *Advances in Topical antifungal therapy.,* Springer verlag, Berlin, (1986), pp. 120–124.

The art described above does not, however, teach the use of imidazole derivatives in regulating vitamin D metabolism or growth and differentiation in the skin or skin cell cultures. Furthermore, the art does not describe cosmetic composition containing an azole in combination with a short-chain lipid. Combinations of short chain lipids with azoles do not appear to have been described to potentlate the benefits of vitamin D in any system.

Accordingly, it is an object of the present invention to provide compositions for treatment of skin, while avoiding the disadvantages of prior art.

It is another object of the present invention to provide a skin treatment composition containing an azole in combination with a short-chain lipid.

It is another object of the invention to provide a method for treating or preventing the appearance of wrinkled, flaky, aged, photodamaged skin or skin disorders, such as acne, xerosis, ichthyosis and psoriasis.

These and other objects of the invention will become more apparent from the detailed description and examples which follow.

SUMMARY OF THE INVENTION

The above objects are attained by the present invention which includes, in part, a composition containing:

(i) from about 0.0001% to about 50 wt. % of an azole;

(ii) from about 0.0001% to about 50 wt. % of a lipid material selected from the group consisting of short-chain ceramides, pseudoceramides, neoceramides, and mixtures thereof; and (iii) a cosmetically acceptable vehicle for the azole and the lipid material.

Preferably, the ratio of the lipid ingredient to the azole is in the range of from about 1:100 to about 100:1, most preferably the ratio is about 1:1.

The vehicle enables the azole and the lipid material to be dispersed onto the skin and distributed therein. According to the invention, the azole is employed in combination with the lipid material selected from short chain (i.e., $C_1$–$C_{10}$) ceramides, pseudoceramides and neoceramides, (i.e., R in ceramides of Formula II or $R_6$ in pseudoceramides of Formula III or $R_{11}$ in neoceramides of Formula IV, contains from 1 to 10 carbon atoms), in order to attain a synergistic keratinocyte prodifferentiating activity.

The present invention also includes a method of improving or preventing the appearance of wrinkled, flaky, aged, photodamaged skin and treating skin disorders, which method includes applying to the skin a composition containing an azole and a lipid ingredient.

Compositions of the invention are intended for topical application to mammalian skin which is already in dry, flaky, wrinkled, aged, photodamaged condition or which suffers from a skin disorder, or, in the alternative, the inventive compositions may be applied prophylactically to normal healthy skin to prevent or reduce the deteriorative changes.

DETAILED DESCRIPTION OF THE INVENTION

The inventive compositions contain, as a first essential ingredient, an azole. Suitable azoles have Formula I.

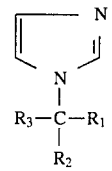

where $R_1$, $R_2$ and $R_3$ are H or ethonyl, thioyls, alkyl containing 1–12 carbon atoms, aryl group, aryl group containing 1–5 halogen atoms, heterocyclic group containing nitrogen and/or oxygen atoms and mixtures thereof.

Examples of suitable azoles include but are not limited to econazole, clotrimazole, bifonazole, miconazole, ketoconazole, butoconazole, climbazole, sulconazole, liarazole, and mixtures thereof.

Preferably, in order to optimize performance (specifically, to optimize the keratinocyte differentiation) the azole is selected from the group consisting of econazole, clotrimazole, bifonazole, and mixtures thereof, In general, the amount of the azole is in the range of from about 0.0001% to about 50% by weight of the composition. Preferably, in order to lower cost and maximize the synergistic effect, the amount of the azole is in the range of from about 0.001% to about 1%, most preferably in the range of from 0.0001% to 0.1%.

Lipid Component

The second essential ingredient of the inventive compositions is a lipid. The lipid component is chosen from ceramides, pseudoceramides, neoceramides and mixtures thereof.

Ceramides

Ceramides are preferably selected from ceramides having structure (II):

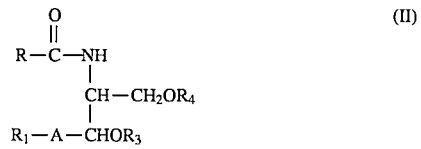

where

A represents —$CH_2$—; —CHOH—; or —CH=CH—

R is a linear or branched saturated or unsaturated, aliphatic hydrocarbon group having from 1 to 10 carbon atoms which may contain a hydroxyl group:

$R_1$ represents a linear or branched, saturated or unsaturated, hydroxylated or non-hydroxylated aliphatic hydrocarbon group having from 8 to 28 carbon atoms or a phenyl group;

$R_3$ and $R_5$ individually represent H, a phosphate group or a sulphate group;

$R_4$ represents H, a phosphate group, a sulphate group or a sugar group.

Further identification of ceramide structures may be found in U.S. Pat. No. 4,950,688 (Bowser et al.), herein incorporated by reference. Ceramides having the structure (II) are naturally occurring and can be isolated from a suitable plant source or from animal tissue such as pig skin or neural tissue. Ceramides can also be synthesized according to procedures described in one of the following references:

Shoyama, Y. et al., *Journal of Lipid Res.,* Vol. 19, (1978), pp. 250–258.

Hino, T. et al., *Journal of Chem. Soc. Parkin. Tran. J.* (1986), p. 1687.
Junana, R. et al., *Hel. Chem, Acta,* Vol. 69(1986), p. 368.
Kiso, M. et al., *J. Carbohydrate Chem.,* Vol. 5, (1986), p. 93.
Kolke, K. et al., *Carbohyd. Res.,* Vol. 158, (1986), p. 113.
Schmidt, R. et al., *Tetrahedro. Let.,* (1986), pp. 481.

Ceramides may also be mixtures of different stereoisomers, (i.e., D-threo, L-threo, D-erythro and L-erythro). Most preferred, in order to attain the synergy with the azole are short chain ceramides wherein A is —$CH_2$, $R_4$ is hydrogen, $R_3$ is hydrogen, and $R_1$ contains from 8 to 20 carbon atoms.

Pseudoceramides Pseudoceramides (i.e., synthetic ceramide-like structures) are preferably selected from pseudoceramides having the general structure (III):

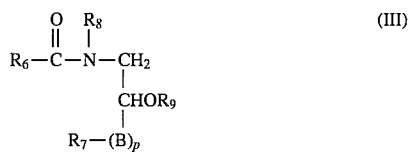

(III)

where

B represents —$OCH_2$— or —CHCHOH or —$CH_2$;

$R_6$ represents a linear or branched, saturated or unsaturated, or hydroxylated aliphatic hydrocarbon group having from 1 to 10 carbon atoms or the subgroup (2) as described above;

$R_7$ represents a linear or branched, saturated or unsaturated or hydroxylated hydrocarbon group having from 8 to 28 carbon atoms or a phenyl group;

$R_8$ represents H, or a subgroup —$(CH_2)_cR_{10}$, or a subgroup having the structure (4), where c is an integer of from 1 to 6, $R_{10}$ is —OH or a phosphate group, or a sulfate group, or a sugar group;

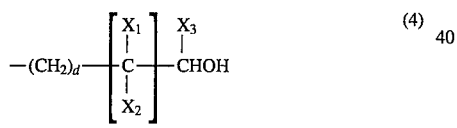

(4)

where $X_1$, $X_2$ and $X_3$ each individually represent H, a $C_{1-5}$ alkyl or a $C_{1-5}$ hydroxyalkyl;

d is 0 or an integer of from 1 to 4; and p is 0 or 1;

$R_9$ represents H, a phosphate group, a sulphate group or a sugar group.

Pseudoceramides may be synthesized according to the procedures described in U.S. Pat. No. 4,778,823, or U.S. Pat. No. 5,198,210, or U.S. Pat. No. 5,206,020, all of which are incorporated by reference herein.

Preferably, in order to attain synergy and minimize cost, pseudoceramides are employed wherein $R_8$ is $CH_2CH_2OH$, $R_9$ is hydrogen, B is —$OCH_2$ or $CH_2$, and $R_7$ contains from 10 to 22 carbon atoms.

Neoceramides

Neoceramides, like pseudoceramides, are synthetic ceramide-like structures. Neoceramides, however, contain more localized polar groups than pseudoceramides. Neoceramides are selected from neoceramides having the general structure (IV):

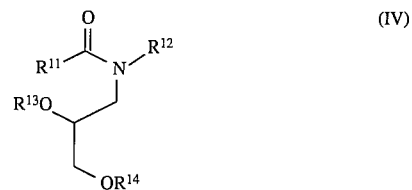

wherein $R^{11}$ is a linear or branched, saturated, or unsaturated, aliphatic hydrocarbon group having from 1 to 10 carbon atoms which may contain a hydroxy group, ester group and/or an ether group; $R^{12}$ is a linear branched, saturated or unsaturated aliphatic hydrocarbon group having from 7 to 48 carbon atoms; $R^{13}$ and $R^{14}$ are the same or different and each is selected from the group consisting of hydrogen, a sulfate group, a phosphate group, or a sugar group.

The neoceramide can be prepared in two steps: first, neosphingosine of formula (V) is prepared by reacting halopropanediol or glycidol with an alkylamine ($R^{12}NH_2$). In a preferred embodiment of the invention, the alkylamine is preferably a primary amine and it contains from 1 to 48, preferably from 7 to 26, most preferably from 11 to 18 carbon atoms.

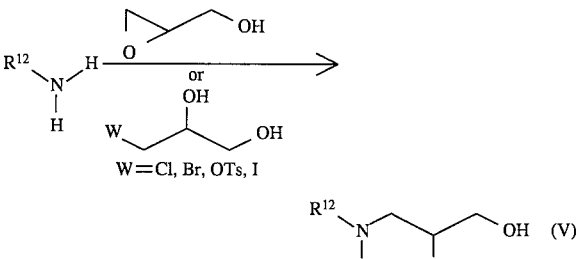

When glycidol is employed, 0.8–2.0 equivalents, preferably 1.0 equivalent, of glycidol is added, slowly to the stirring mix of one equivalent of the alkylamine in a solvent. Suitable solvents include but are not limited to ethanol, methanol, isopropanol or water; the reaction may also be performed neat. The mixture is preferably heated, preferably from 25°–100° C., for a sufficient time, e.g., 1–48 hours. After the completion of the reaction, neosphingosine is isolated. When halopropanediol (one equivalent) is employed, suitable halopropanediols include but are not limited to bromopropanediol, chloropropanediol, 3-tosylpropanediol and iodopropanediol, is reacted with preferably one equivalent of alkylamine in presence of 1–3 equivalent of base (e.g., potassium carbonate, etc.) in a solvent. The same solvent may be employed as described above. A similar work up is employed to isolate neosphingosine of formula V.

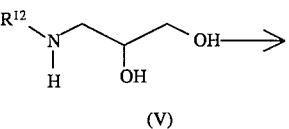

(V)

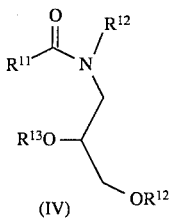

(IV)

The resulting neosphingosine of formula V may be converted into a neoceramide of formula IV by reacting the neosphingosine with an acyl chloride, acyl anhydride, fatty acid (with or without catalyst) or fatty acid ester.

In a preferred embodiment of the invention, $R^{11}$ is preferably a primary alkyl group containing from 1 to 16, most preferably from 1 to 10 carbons atoms, $R^{12}$ contains from 7 to 24 carbon atoms, $R^{13}$ is hydrogen and $R^{14}$ is hydrogen.

Specific preferred examples of ceramides, pseudoceramides and neoceramides are represented by the following Formulae below:

Neoceramide:

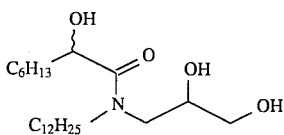 (K)

Ceramides:

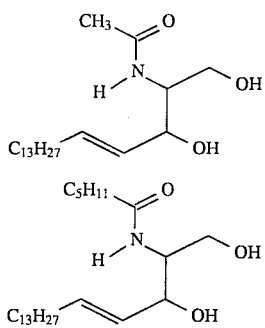

(A)

(B)

Pseudoceramides:

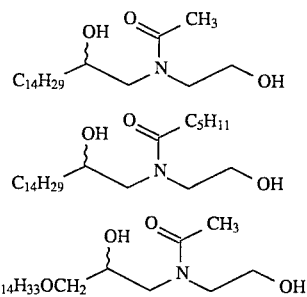

(C)

(D)

(E)

Neoceramides:

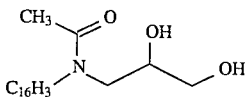 (F)

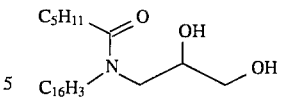 (G)

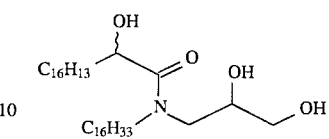 (H)

Pseudoceramides
N-(2-hydroxyoctadecyl)-N-(2-hydroxyethyl)propanamide
N-(2-hydroxyhexadecyl)-N-(2-hydroxyethyl)heptanamide
N-(2-hydroxyoctadecyl)-N-(2-hydroxyethyl)ethanamide
N-(2-hydroxyoctadecyl)-N-(2-O-glucopyranosyl)ethylpentanamide
N-(2-hydroxydodecyl)-N-(2-hydroxyethyl)hexanamide
N-(2-hydroxydodecyl)-N-(2-hydroxyethyl)-2butylhexanamide
N-(2-hydroxyhexadecyl)-N-(2-hydroxyethyl)ethanamide
N-(2-hydroxydodecyl)-N-(2-hydroxyethyl)-2-hydroxyhexanamide
N-(2-hydroxytetraadecyl)-N-(2-hydroxyethyl)propanamide
N-(2-hydroxyoctadecyl)-N-(2-phosphethyl)butanamide
N-(2-hydroxyoctadecyl)-N-(2-hydroxyethyl)-2-hydroxypropanamide
N-(2-hydroxydecyl)-N-(2-hydroxyethyl)butanamide
N-(2-hydroxy-3-octadecyloxypropyl)-N-(2-hydroxyethyl)butanamide
N-(2-hydroxy-3-hexadecyloxypropyl)-N-(2-hydroxyethyl)ethanamide
N-(2-hydroxy-3-dodecyloxypropyl)-N-(2-sulfohydroxyethyl)decanamide
N-(2-hydroxy-3-decyloxypropyl)-N-(2-hydroxyethyl)hexanamide
N-(2-hydroxy-3-dodecyloxypropyl)-N-(2-hydroxyethyl)butanamide
N-(2-hydroxy-3-dodecyloxypropyl)-N-(2-hydroxyethyl)propanamide
N-(2-hydroxy-3-hexadecyloxypropyl)-N-(2-hydroxyethyl)-2-methylpropanamide
N-(2-hydroxy-3-tetraadecyloxypropyl)-N-(2-hydroxyethyl)ethanamide
N-(2-hydroxy-3-nonanyloxypropyl)-N-(2-hydroxyethyl)propanamide
N-(2-hydroxy-3-dodecyloxypropyl)-N-(2-hydroxyethyl)heptanamide
N-(2-hydroxy-3-hexadecyloxypropyl)-N-(2-phosphoethyl)hexadecanamide
N-(2-hydroxy-3-dodecyloxypropyl)-N-(2-hydroxyethyl)propanamide
N-(2-hydroxy-3-octadecyloxypropyl)-N-(2-)-glucopyranosyl)ethyl-2-hydroxypropanamide
N-(2-hydroxy-3-octyloxypropyl)-N-(2-hydroxyethyl)pentanamide Neoceramides
N-(2,3-dihydroxypropyl)-N-(hexadecyl)butanamide
N-(2,3-dihydroxypropyl)-N-(tetradecyl)ethanamide
N-(2,3-dihydroxypropyl)-N-(hexadecyl)-2-hydroxypropanamide
N-(2,3-dihydroxypropyl)-N-(octadecyl)butanamide
N-(2,3-dihydroxypropyl)-N-(2-ethylhexadecyl)hexanamide
N-(2,3-dihydroxypropyl)-N-(hexadecyl)-2-hydroxyoctanamide
N-(2,3-dihydroxypropyl)-N-(3-methylhexadecyl)ethanamide N-(2,3-dihydroxypropyl)-N-(dodecyl)butanamide
N-(2,3-dihydroxypropyl)-N-(hexadecyl)-2-hydroxyhexanamide
N-(2-hydroxy-3-O-glucopyranosylpropyl)-N-(hexadecyl)octanamide
N-(2-hydroxy-3-phosphopropyl)-N-(octadecyl)ethanamide
N-(2-hydroxy-3-sulfopropyl)-N-(hexadecyl)butanamide
N-(2-hydroxy-3-O-glucopyranosylpropyl)-N-(hexadecyl)decanamide
N-(2,3-dihydroxypropyl)-N-(heptadecyl)ethanamide
N-(2,3-dihydroxypropyl)-N-(3-methylhexadecyl)ethanamide
N-(2,3-dihydroxypropyl)-N-(heptadecyl)butanamide
N-(2,3-dihydroxypropyl)-N-(6-dodecenyl)hexadecanamide
N-(2,3-dihydroxypropyl)-N-(2-methylhexadecyl)2-hydroxyetahnamide
N-(2,3-dihydroxypropyl)-N-(octadecyl)2-hydroxypropanamide
N-(2-hydroxy-3-O-glucopyranosylpropyl)-N-(heptadecyl)ethanamide
N-(2-hydroxy-3-sulfopropyl)-N-(dodecyl)heptanamide
N-(2,3-dihydroxypropyl)-N-(tetradecyl)-4-hydroxybutanamide
N-(2,3-dihydroxypropyl)-N-(linoleyl)ethanamide
N-(2,3-dihydroxypropyl)-N-(oleyl)-2-hydroxyheptanamide
N-(2,3-dihydroxypropyl)-N-(octadecyl)-3-hydroxybutanamide
N-(2-phospho-3hydroxypropyl)-N-(heptadecyl)butanamide
N-(2,3-dihydroxypropyl)-N-(2-methylheptadecyl)propanamide
N-(2,3-dihydroxypropyl)-N-(3-ethylheptadecyl)butanamide
N-(2-sulfo-3-hydroxypropyl)-N-(1-octadecyl)ethanamide
N-(2,3-dihydroxypropyl)-N-(octadecyl)propanamide
N-(2,3-dihydroxypropyl)-N-(dodecyl)decanamide
N-(2,3-dihydroxypropyl)-N-(3-ethyldodecyl)butanamide
N-(2,3-dihydroxypropyl)-N-(oleyl)-2-hydroxypropanamide
N-(2,3-dihydroxypropyl)-N-(linoleyl)-2-hydroxyheptanamide
N-(2,3-dihydroxypropyl)-N-(dodecyl)-2-hydroxyoctanamide
N-(2,3-dihydroxypropyl)-N-(hexadecyl)-2-methylheptanamide
N-(2,3-dihydroxypropyl)-N-(octadecyl)-2-hydroxypentanamide
N-(2,3-dihydroxypropyl)-N-(2-methylhexadecyl)-2-hydroxyheptanamide
N-(2,3-dihydroxypropyl)-N-(lioleyl)-2-hydroxypropanamide
N-(2,3-dihydroxypropyl)-N-(tetreadecyl)ethanamide The amount of the lipid material in the composition is in the range of from about 0.0001% to about 50% by weight of the composition, preferably from about 0.001% to about 10%, most preferably from about 0.0001% to about 0.1%.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin, hair and/or nails.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the emulsion, and can, in the absence of other cosmetic adjuncts, form the balance of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

In a preferred embodiment of the invention, the inventive compositions further include at least one of the following ingredients which are particularly effective in combination with azole and the lipid component:

Hydroxyacids—enhance proliferation and increases ceramide biosynthesis in keratinocytes, increase epidermal thickness, and increase desquamation of normal skin resulting in smoother, younger looking skin.

The hydroxy acid can be chosen from α-hydroxy acids, β-hydroxyacids, other hydroxycarboxylic acids (e.g., dihydroxycarboxylic acid, hydroxydicarboxylic, hydroxytricarboxylic) and mixtures thereof or combination of their stereoisomers (DL, D or L).

Preferably the hydroxy acid (ii) is chosen from α-hydroxy acids having the general structure (13):

$$\begin{matrix} \text{OH} \\ | \\ \text{MCHCOOH} \end{matrix} \quad (13)$$

where

M is H— or $CH_3$ $(C_fH_g)_h$—, f is an integer of from 1 to 27, g is an integer of from 2 to 54, and h is 0 or 1.

Even more preferably, the hydroxy acid is chosen from 2-hydroxyoctanoic acid, hydroxylauric lactic acid, and glycolic acid, and mixtures thereof. When stereo isomers exist, L-isomer is most preferred.

The keto acids can be chosen from α-keto acids, β-keto acids and mixtures thereof.

A particularly preferred α-keto acid is 2-keto octanoic acid.

Preferably the amount of the hydroxy acid component (ii) present in the composition according to the invention is from 0.01% to 20%, more preferably from 0.05% to 10% and most preferably from 0.1% to 3% by weight.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol® from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, anti-acne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,507, incorporated by reference herein.

METHODS

Methodology Used for Determining the Rate of DNA Synthesis in Keratinocytes After Treatment With Various Actives 1. Normal human keratinocytes isolated from neonatal foreskins by trypsin treatment were grown in DME medium/ 10% fetal calf serum in the presence of irradiated 3T3 mouse fibroblasts for establishing dividing keratinocyte colonies. Keratinocytes were grown under the above condition until their third passage.

2. For the experiments, third passage keratinocytes were plated into a serum-free keratinocyte growth medium (KSFM; obtained from Life Technologies, Grand Island, N.Y.) containing 0.09 mM calcium. 20,000 to 30,000 cells were plated into each well of 24 well cell culture plates and grown for 5 days, until the cells reach about 80% confluence.

3. Medium was changed to fresh medium and the various test materials were added to the medium from an ethanolic stock solution (10:00 AM). The final ethanol concentration in the cultures was kept below 0.2%. Control cultures received no tested material but were dosed with 0.2% ethanol. Each compound or combination was tested in three separate wells. By 4:00 PM, 1 uCi of $^3$H-thymidine (Amersham Corp., Sp activity 40 Ci/mmol) was added to the 1 ml medium in each well. The cells were incubated overnight and 24 hours later (10:00 AM next day) the amount of $^3$-thymidine associated with the cellular DNA of keratinocytes was assessed as described below.

4. The medium was aspirated, and the wells washed with 1 ml phosphate-buffered saline. The DNA and proteins of the cells in the plate were then precipitated by adding 1 ml of ice-cold 10% trichloroacetic acid (TCA). The plates were left on ice for 30 minutes to complete the precipitation process. TCA was then aspirated and each well was then washed four times with 5% TCA. The plates were then dried on a filter pad and the cells in the wells were dissolved in 0.5 ml of 0.1N sodium hydroxide. The sodium hydroxide was then neutralized using 0.1N hydrochloric acid and the solution (1 ml total volume) was then transferred to a scintillation vial. 50 μl samples from each vial were used for protein assay using BCA protein assay reagent obtained from Pierce Chemical Company. 8 ml of a scintillation fluid (Ecolume) was added to the rest of the solution in the vial, and the vials were counted in a scintillation counter to determine the amount of radioactivity in each vial. The DNA synthesis rate was then calculated as cpm $^3$H thymidine incorporated into total cellular DNA/microgram of cell protein for each individual well. Mean and standard deviation for each group was also calculated. These numbers were also expressed as percent of control wells which did not receive any azole or lipid.

5. All lipids listed in Tables 1–5 below were synthesized in-house. Azoles were obtained from Sigma Chemical Co., St. Louis, Mo. Other imidazole compounds were also purchased from Sigma. Imidaz® and Nikkol® were obtained from Mona Chemicals, Paterson, N.J.

Method for Vitamin D Metabolism in Keratinocytes

80% confluent keratinocytes were incubated with 0.05 uCi of $^3$H-25D or $^3$H-1,25D for two hours or 20 hours in the presence of 1–100 uM of the different compounds. Reaction was stopped by addition of methanol and the cells and medium were extracted using chloroform:methanol. The chloroform layer was separated, dried and spotted on TLC plates. TLC was run in chloroform (46.5): methanol (3.25): acetic acid (0.25) using both radioactive and nonradioactive standards. The amount of radioactivity in each lane was quantitated using the BioScan radioactive plate reader. The amount of radioactivity remaining in the peak area of 25D and 1,25D were calculated as % of control. The % remaining was subtracted from 100 to get the % degradation of the metabolites. Data of single experiments or mean ± range of duplicate wells are shown.

EXAMPLE 1

AZOLES INHIBIT VITAMIN D METABOLISM IN KERATINOCYTES

A. Comparison of Different Imidazole Compounds on their Effects on Vitamin D Metabolism In this preliminary experiment, to screen for the imidazole compounds which may be useful as inhibitors of vitamin D degradation, different classes of imidazole compounds were compared for their effects on vitamin D metabolism.

TABLE 1

| Class of compounds | Name of compound | Concentration (uM) | % degradation (25D) | % degradation(1,25D) |
| --- | --- | --- | --- | --- |
| — | None | — | 100 | 95.6 |
| Antimicrobial Azoles | Econazole | 10 uM | 5 | 2 |
| Antimicrobial Azoles | Clotrimazole | 10 uM | 5 | 2 |
| Antimicrobial Azoles | Bifonazole | 10 uM | 15 | 56 |
| Antimicrobial Azoles | Miconazole | 10 uM | 54 | 70 |
| Triazoles | Triazole | 100 uM | 48 | 86 |
| Simple imidazole | Diamino benzimidazole | 100 uM | 72 | 92 |
| Imidazole/thiazole containing vitamins | Thiamine | 100 uM | 85 | 77 |
| Imidazole/thiazole containing vitamins | folic acid | 100 uM | 78 | 95 |
| Imidazole containing amino acid | L-Tryptophan | 100 uM | 83 | 100 |
| Imidazole containing urea | Nikkol | 100 uM | 94 | 72 |
| Imidazole containing urea | Imdaz | 100 uM | 77 | 63 |
| Non-imidazole cytochrome P450 inhibitor | menadione (vitamin K1) | 100 uM | 89 | 93 |

The results in Table 1 indicate that azoles inhibited 1,25D and 25D metabolism. Of the azoles tested, econazole and clotrimazole are the most potent.

B. Effect of 1 uM Azoles on Inhibition of Vitamin D Metabolism

To confirm the inhibitory effect of azoles on vitamin D metabolism, the following experiment was conducted using 1 uM of the different azoles using 20 hour incubation.

The experimental protocol was the same as Example 1 except that 1 uM azoles were used in this experiment and each azole was run in duplicate. The data are expressed as mean of % degradation of 25D or 1,25D. The range is also given in parenthesis.

TABLE 2

| Azole (1 uM) | 25D degradation (%) | 1,25D degradation (%) |
| --- | --- | --- |
| None | 84.4 (73–96.9) | 74.2 (64.1–84.5) |
| Econazole | 54.1 (44.3–63.9) | 46.8 (45.1–48.6) |
| Clotrimazole | 47.4 (42.6–52.2) | 29.5 (21.8–37.2) |
| Bifonazole | 41.2 (35.4–47.1) | 37.0 (25.4–48.6) |
| Miconazole | 38.7 (35.4–42.0) | 75.8 (69.9–81.8) |

TABLE 2-continued

| Azole (1 uM) | 25D degradation (%) | 1,25D degradation (%) |
| --- | --- | --- |
| Triazole | 72.4 (66.8–78.0) | 75.6 (72.9–78.3) |
| Nikkol | 94.7 (94.1–95.4) | 71.8 (61.2–82.3) |
| Imidaz | 77.6 (77.4–77.9) | 63.0 (54.7–71.3) |

As in the previous experiment, econazole, clotrimazole and bifonazole were found to be very effective in blocking both 25D and 1,25D degradation. Miconazole was effective with 25D but did not block 1,25D degradation in this experiment.

C. Time Dependence for the Effect of Azoles

A time course of the effects of azoles on vitamin D degradation indicated a lag period of at least two hours before the effects of the azoles are observed. For example, the three most effective of the azoles, Econazole, Clotrimazole and Bifonazole were ineffective to block both 25D and 1,25D metabolism in 2 hours while they were very effective in 20 hours.

TABLE 3

| Azole (10 uM) | 25D (% degradation) (2 hours) | 25D (% degradation) (20 hours) | 1,25D (% degradation) (2 hours) | 1,25D (% degradation) (20 hours) |
| --- | --- | --- | --- | --- |
| Econazole | 92 | 5 | 78 | 2 |
| Clotrimazole | 79 | 5 | 77 | 2 |
| Bifonazole | 89 | 15 | 83 | 56 |

The above three experiments clearly indicate that the anti-microbial azoles inhibit vitamin D degradation of keratinocytes very effectively, even at 1 uM levels. Optimal inhibition occurs only after a time lag of two hours treatment with the azoles.

EXAMPLE 2

SYNERGY BETWEEN THE AZOLES AND C2 CERAMIDES ON KERATINOCYTE GROWTH INHIBITION IN THE PRESENCE OF 100 nM 1,25D

Azole compounds not only inhibit further degradation of 1,25D, but they also inhibit the conversion of 25D to 1,25D. Therefore, Examples below 1,25D was used in combination with azoles and short chain lipids to show the potentiation of growth inhibition (differentiation benefit). Rationale for using 1,25D is that in in vivo situation, these azoles will inhibit the endogenous degradation of the 1,25D which is obtained from the circulation. Azoles will act in keratinocytes to increase the endogenous levels of 1,25D within cells. Keratinocytes (70% confluent) were incubated with 10 uM of the different azoles in the presence of 100 nM 1,25D. One of the groups was treated with 5 uM of ceramide of Formula A in the medium. After four hours, all the wells were treated with 1 uCi $^3$H-thymidine and the rate of DNA synthesis was estimated as described in the methods. The summary of the results are shown in Table 4.

TABLE 4

| Azole (10 uM) | Control (only 100 nM 1,25D) | 100 nM 1,25D + 5 uM ceramide Formula A |
| --- | --- | --- |
| No azole | 100 + 8.1 | 81.1 + 16.5 |
| Econazole | 64.5 + 3.9 | 22.5 + 2.4* |
| Bifonazole | 75.8 + 4.3 | 44.4 + 7.3* |
| Miconazole | 42.8 + 1.8 | 17.5 + 3.3* |
| Clotrimazole | 35.2 + 6.5 | 19.5 + 0.77* |
| Imidaz | 103.6 + 10.1 | 88.4 + 11.1 |
| Triazole | 103.9 + 35.6 | 62.5 + 15.8 |

*Synergistic effect between azoles and ceramides. (Detailed statistical analysis in Tables 4A–4F.)

All the azoles which blocked 1,25D catabolism show good inhibition of growth in the presence of 100 nM 1,25D. In combination with ceramide of Formula A, all these azoles showed synergistic effect on growth inhibition above that of ceramide controls. Imidaz and triazole, poor inhibitors of 1,25D degradation, are also poor inhibitors of keratinocyte growth by themselves and in combination with the ceramide. Thus, this data clearly show the synergy between azole compounds and the ceramide on keratinocyte proliferation. Combination of azoles with 1,25D and the ceramide shows maximum inhibition of DNA synthesis and shows synergy over either compound alone or 1,25D and the ceramide alone. The statistical analysis of the synergy is shown in the detailed analysis of the data for each azole as shown in Tables 4A to 4F.

TABLE 4A

| | Synergy between Econazole and Ceramide of Formula A | | | |
| --- | --- | --- | --- | --- |
| Treatment | DNA synthesis (% control) | p value vs. control | p value vs. ceramide | p value vs. azole |
| Control | 146684 + 11863 (100%) | 1.000 | 0.0746 | .0024 |
| Ceramide | 108753 + 24719 (74.14%) | 0.074 | 1.000 | .3923 |
| Econazole | 94719 + 5732 (64.57%) | 0.0024 | .3923 | 1.000 |
| Econazole + Ceramide | 33044 + 3539 (22.53%) | 0.00009 | .0063 | .00009 |

TABLE 4B

Synergy Between Bifonazole and Ceramide of Formula A

| Treatment | DNA synthesis (% control) | p value vs. control | p value vs. ceramide | p value vs. azole |
|---|---|---|---|---|
| Control | 146684 + 11863 (100%) | 1.000 | 0.0746 | .0103 |
| Ceramide | 108753 + 24719 (74.14%) | 0.074 | 1.000 | .8733 |
| Bifonazole | 111256 + 6355 (75.8%) | .0103 | .8733 | 1.000 |
| Bifonazole + Ceramide | 65156 + 10694 (44.4%) | 0.0009 | .0486 | .00303 |

TABLE 4C

Synergy Between Miconazole and Ceramide of Formula A

| Treatment | DNA synthesis (% control) | p value vs. ceramide | p value vs. azole | p value vs. |
|---|---|---|---|---|
| Control | 146684 + 11863 (100%) | 1.000 | 0.0746 | .00028 |
| Ceramide | 108753 + 24719 (74.14%) | 0.074 | 1.000 | .0328 |
| Miconazole | 62806 + 2649 (42.8%) | .00028 | .0328 | 1.000 |
| Miconazole + Ceramide | 25599 + 4953 (17.4%) | .00008 | .00464 | .00033 |

TABLE 4D

Synergy Between Clotrimazole and Ceramide of Formula A

| Treatment | DNA synthesis (% control) | p value vs. control | p value vs. ceramide | p value vs. azole |
|---|---|---|---|---|
| Control | 146684 + 11863 (100%) | 1.000 | 0.0746 | .00027 |
| Ceramide | 108753 + 24719 (74.14%) | 0.074 | 1.000 | .0181 |
| Clotrimazole | 51610 + 6735 (35.2%) | .00027 | .0181 | 1.000 |
| Clotrimazole + Ceramide | 28642 + 803 (19.5%) | .000067 | .00495 | .00421 |

TABLE 4E

Absence of Synergy Between Imidaz and Ceramide of Formula A

| Treatment | DNA synthesis (% control) | p value vs. control | p value vs. ceramide | p value vs. azole |
|---|---|---|---|---|
| Control | 146684 + 11863 (100%) | 1.000 | 0.0746 | .6486 |
| Ceramide | 108753 + 24719 (74.14%) | 0.074 | 1.000 | .0599 |
| Imidaz | 152082 + 14856 (103.7%) | .6486 | .0599 | 1.000 |
| Imidaz + Ceramide | 129713 + 16301 (88.4%) | .2185 | .2874 | .1538 |

TABLE 4F

Absence of Synergy Between Triazole and Ceramide of Formula A

| Treatment | DNA synthesis (% control) | p value vs. control | p value vs. ceramide | p value vs. azole |
|---|---|---|---|---|
| Control | 146684 + 11863 (100%) | 1.000 | 0.0746 | .8607 |
| Ceramide | 108753 + 24719 (74.14%) | 0.074 | 1.000 | .2601 |
| Triazole | 152464 + 52212 (103.9%) | .860 | .260 | 1.000 |
| Triazole + Ceramide | 91701 + 23198 (62.5%) | .0216 | .4327 | .1392 |

EXAMPLE 3

SYNERGY BETWEEN AZOLE AND OTHER SHORT CHAIN CERAMIDES AND CERAMIDE ANALOGUES

To determine whether the synergy seen above between Formula A ceramide and the different azoles also exists between other ceramide compounds and azoles, the following experiment was carried out. Keratinocytes were incubated with 1 or 10 uM of Econazole in the presence of 1 uM of the different ceramide analogues and 100 nM 1,25D in the medium. Thymidine incorporation was measured with an overnight incubation as described in Example 2. Summary of the data is given below (Table 5) and the detailed statistical analysis is shown in Table 5A to 5I.

TABLE 5

Summary of synergy between Econazole and various ceramide analogues on keratinocyte DNA synthesis. (Data expressed as % of the corresponding controls)

| Ceramide (1 uM) | No azole | 1 uM Econazole | 10 uM Econazole |
|---|---|---|---|
| No ceramide | 100 + 16 | 100 + 20.2 | 100 + 23.2 |
| Formula A | 97 + 32 | 75.9 + 23.3 | 38.2 + 13.9* |
| Formula B | 126.6 + 17.8 | 123.9 + 30.3 | 61.7 + 17* |
| Formula F | 90.3 + 21.4 | 84.3 + 1.96 | 40.9 + 9.0* |
| Formula G | 102.8 + 14.4 | 84.8 + 12.7 | 28.2 + 15.2* |
| Formula K | 100.2 + 9.6 | 82.9 + 16.9 | 38.7 + 14.8* |
| Formula H | 89.5 + 5.6 | 113.9 + 24.6 | 45.2 + 20.1* |
| Formula C | 77.7 + 7.4 | 78.0 + 15.1 | 47.2 + 33.6 |

TABLE 5-continued

Summary of synergy between Econazole and various ceramide analogues on keratinocyte DNA synthesis. (Data expressed as % of the corresponding controls)

| Ceramide (1 uM) | No azole | 1 uM Econazole | 10 uM Econazole |
|---|---|---|---|
| Formula D | 69.5 + 11.3* | 97.0 + 19.5 | 28.8 + 3.9* |
| Formula E | 104.3 + 17.7 | 99.8 + 19.1 | 20.5 + 12.9* |

*Synergistic effect between Econazole and the different analogues. (detailed analysis in Tables 5A–5I).

The results indicate that in the absence of azole, none of the ceramide analogues (except Formula D) was significantly inhibitory at 1 uM level. In the presence of 1 uM econazole also there was no significant growth inhibition for any of the azoles. However, at 10 uM levels of econazole, all the ceramide analogues were significantly inhibitory, suggesting a synergy of action between 10 uM econazole and ceramide analogues. In the previous experiment also only 10 uM levels of the different azoles showed synergistic inhibition of growth with Formula H ceramides (1 uM levels had no effect, data not shown).

Detailed statistical analysis of the data of Table 5 are shown in the Tables 5A to 5I given below. The data of 10 uM econazole treatment with 1 uM of the different ceramide analogues are analyzed in detail, since the 1 uM econazole and 1 uM ceramide analogue showed no synergy (Table 5 above).

TABLE 5A

Synergy Between Econazole and Ceramide of Formula A

| Treatment | DNA synthesis (% control) | p value vs. control | p value vs. azole | p value vs. ceramide |
|---|---|---|---|---|
| Control | 29952 + 5534 (100%) | 1.000 | .0125 | .9163 |
| Econazole | 15147 + 4337 (50.5%) | .0125 | 1.000 | .0962 |
| Ceramide | 29272 + 11126 (97.7%) | .9163 | .0962 | 1.000 |
| Econazole + Ceramide | 5792 + 2435 (19.3%) | .0002 | .0143 | .0062 |

TABLE 5B

Synergy Between Econazole and Ceramide of Formula B

| Treatment | DNA synthesis (% control) | p value vs. control | p value vs. azole | p value vs. ceramide |
|---|---|---|---|---|
| Control | 29952 + 5534 (100%) | 1.000 | .0125 | .1405 |
| Econazole | 15147 + 4337 (50.5%) | .0125 | 1.000 | .0074 |
| Ceramide | 37927 + 6562 (126%) | .1405 | .0074 | 1.000 |
| Econazole + Ceramide | 9345 + 2984 (31.2%) | .0006 | .0877 | .0005 |

TABLE 5C

Synergy Between Econazole and Neoceramide of Formula F

| Treatment | DNA synthesis (% control) | p value vs. control | p value vs. azole | p value vs. ceramide |
|---|---|---|---|---|
| Control | 29952 + 5534 (100%) | 1.000 | .0125 | .5878 |
| Econazole | 15147 + 4337 (50.5%) | .0125 | 1.000 | .0832 |

TABLE 5C-continued

Synergy Between Econazole and Neoceramide of Formula F

| Treatment | DNA synthesis (% control) | p value vs. control | p value vs. azole | p value vs. ceramide |
|---|---|---|---|---|
| Neoceramide | 27051 + 7858 (90.3%) | .5878 | .0832 | 1.000 |
| Econazole + Neoceramide | 6202 + 1578 (20.7%) | .00017 | .0114 | .0031 |

TABLE 5D

Synergy Between Econazole and Neoceramide of Formula G

| Treatment | DNA synthesis (% control) | p value vs. control | p value vs. azole | p value vs. ceramide |
|---|---|---|---|---|
| Control | 29952 + (100%) | 1.000 | .0125 | .8476 |
| Econazlole | 15147 + 4337 (50.5%) | .0125 | 1.000 | .01679 |
| Neoceramide | 30794 + 5311 (102.8%) | .8476 | .0167 | 1.000 |
| Econazole + Neoceramide | 3583 + 1415 (11.96%) | .00009 | .00369 | .00016 |

TABLE 5E

Synergy Between Econazole and Neoceramide of Formula K

| Treatment | DNA synthesis (% control) | p value vs. control | p value vs. azole | p value vs. ceramide |
|---|---|---|---|---|
| Control | 29952 + 5534 (100%) | 1.000 | .0125 | .1807 |
| Econazole | 15147 + 4337 (50.5%) | .0125 | 1.000 | .0761 |
| Neoceramide | 23958 + 5660 (80%) | .1807 | .0761 | 1.000 |
| Econazole + Neoceramide | 5864 + 2591 (19.6%) | .00022 | .0159 | .0011 |

TABLE 5F

Synergy Between Econazole and Neoceramide of Formula H

| Treatment | DNA synthesis (% control) | p value vs. control | p value vs. azole | p value vs. ceramide |
|---|---|---|---|---|
| Control | 29952 + 5534 (100%) | 1.000 | .0125 | .6031 |
| Econazole | 15147 + 4337 (50.5%) | .0125 | 1.000 | .03408 |
| Neoceramide | 32907 + 8703 (109.8%) | .6031 | .0341 | 1.000 |
| Econazole + Neoceramide | 6763 + 1043 (22.6%) | .00017 | .0121 | .00165 |

TABLE 5G

Synergy Between Econzaole and Pseudoceramide of Formula C55

| Treatment | DNA synthesis (% control) | p value vs. control | p value vs. azole | p value vs. ceramide |
|---|---|---|---|---|
| Control | 29952 + 5534 (100%) | 1.000 | .0125 | .1177 |
| Econazole | 15147 + 4337 (50.5%) | .0125 | 1.000 | .0514 |
| Pseudoceramide | 23288 + 2737 (77.7%) | .1178 | .0514 | 1.000 |
| Econazole + Pseudoceramide | 4652 + 2126 (15.5%) | .00015 | .00776 | .00154 |

TABLE 5H

Synergy Between Econazole and Pseudoceramide of Formual D

| Treatment | DNA synthesis (% control) | p value vs. control | p value vs. azole | p value vs. ceramide |
|---|---|---|---|---|
| Control | 29952 + 5534 (100%) | 1.000 | .0125 | .0359 |
| Econazole | 15147 + 4337 (50.5%) | .0125 | 1.000 | .1297 |
| Pseudoceramide | 20817 + 3928 (69.5%) | .0359 | .1297 | 1.000 |
| Econzaole + Pseudoceramide | 4360 +696 (14.5%) | .000094 | .00393 | .00017 |

TABLE 5I

Synergy Between Econazole and Pseudoceramide of Formula E

| Treatment | DNA synthesis (% control) | p value vs. control | p value vs. azole | p value vs. ceramide |
|---|---|---|---|---|
| Control | 29952 + 5534 (100%) | 1.000 | .0125 | .7612 |
| Econazole | 15147 + 4337 (50.5%) | .0125 | 1.000 | .0121 |
| Pseudoceramide | 31267 + 6143 (104.4%) | .7612 | .0121 | 1.000 |
| Econzole + Pseudoceramide | 3103 + 2263 (10.4%) | .0001 | .0047 | .000135 |

EXAMPLE 4

This example illustrates a high internal phase water-in-oil emulsion incorporating the inventive composition.

| | % w/w |
|---|---|
| Econazole | 0.1 |
| Bifonazole | 0.1 |
| $C_2$ ceramide (formula A) | 0.1 |
| Pseudoceramide (formula D) | 0.1 |
| Fully hydrogenated coconut oil | 3.9 |
| 1,3-dimethyl-2-imidazolidinone | 0.2 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 5

This example illustrates an oil-in-water cream incorporating the inventive composition.

| | % w/w |
|---|---|
| Mizonazole | 0.1 |
| $C_6$ ceramide (formula B) | 0.5 |
| Neoceramide (formula K) | 0.5 |
| Mineral oil | 4 |
| 1,3-dimethyl-2-imidazolidinone | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 6

This example illustrates an alcoholic lotion incorporating the composition according to the invention.

| | % w/w |
|---|---|
| $C_2$ ceramide (formula A) | 0.01 |
| Pseudoceramide (formula E) | 0.01 |
| Clotrimazole | 0.1 |
| Econazole | 0.1 |
| 1,3-dimethyl-2-imidazolidinone | 0.1 |
| Ethanol | 40 |
| Perfume | qs |
| Butylate hydroxy toluene | 0.01 |
| Water | to 100 |

EXAMPLE 7

This example illustrates another alcoholic lotion containing the inventive composition.

| | % w/w |
|---|---|
| Bifonzole | 1 |
| $C_6$ ceramide (formula B) | 1 |
| 1,3-dimethyl-2-imidazolidinone | 0.01 |
| Ethanol | 40 |
| Antioxidant | 0.1 |
| Perfume | qs |
| Water | to 100 |

EXAMPLE 8

This example illustrates a suncare cream incorporating the composition of the invention:

| | % w/w |
|---|---|
| Clotrimazole | 0.1 |
| Bifonazole | 0.1 |
| Pseudoceramide (formula C) | 0.01 |

25
-continued

| | % w/w |
|---|---|
| Neoceramide (formula F) | 0.01 |
| 1,3-dimethyl-2-imidazolidinone | 0.2 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 9

This example illustrates a non-aqueous skin care composition incorporating the inventive combination.

| | % w/w |
|---|---|
| Econazole | 0.1 |
| $C_2$ ceramide | 0.1 |
| 1,3-dimethyl-2-imidazolidinone | 1 |
| Silicone gum SE-30[1] | 10 |
| Silicone fluid 345[2] | 20 |
| Silicone fluid 344[3] | 55.59 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1]A dimethyl silicone polymer having a molecular weight of at least 50,000 and a viscosity of at least 10,000 centistokes at 25° C., available from GEC
[2]Dimethyl siloxane cyclic pentamer, available from Dow Corning Corp.
[3]Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teaching of the disclosure. Accordingly, reference should be made to the following appended claims in determining the full scope of the invention.

What is claimed is:

1. A composition for topical application to human skin, hair or nails, the composition comprising:

i) from about 0.0001 to about 50 wt. % of an azole;

ii) from about 0.0001 to about 50 wt. % of a lipid material selected from the group consisting of:

(a) ceramides having structure (II):

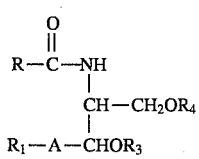

where

A represents —$CH_2$—,

R is a linear or branched saturated or unsaturated, aliphatic hydrocarbon group having from 1 to 10 carbon atoms which may contain a hydroxyl group;

$R_1$ represents a linear or branched, saturated or unsaturated, hydroxylated or non-hydroxylated aliphatic hydrocarbon group having from 8 to 20 carbon atoms;

$R_3$ is hydrogen;

$R_4$ represents hydrogen;

(b) pseudoceramides having the general structure (III):

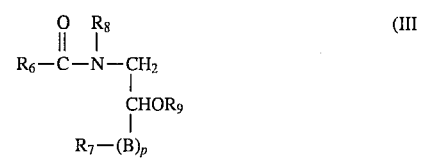

where

B represents —$OCH_2$— or —$CH_2$;

$R_5$ represents a linear or branched, saturated or unsaturated, or hydroxylated aliphatic hydrocarbon group having from 1 to 10 carbon atoms;

$R_7$ represents a linear or branched, saturated or unsaturated or hydroxylated hydrocarbon group having from 10 to 22 carbon atoms;

$R_8$ represents $CH_2CH_2OH$;

$R_9$ represents hydrogen;

(c) neoceramides having the general structure (IV):

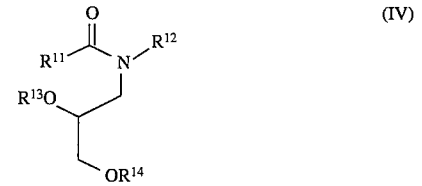

wherein $R^{11}$ is a linear or branched, saturated, or unsaturated, aliphatic hydrocarbon group having from 1 to 10 carbon atoms which may contain a hydroxy group, ester group and/or an ether group;

$R^{12}$ is a linear branched, saturated or unsaturated aliphatic hydrocarbon group having from 7 to 24 carbon atoms;

$R^{13}$ and $R^{14}$ each is a hydrogen;

and mixtures thereof; and iii) a cosmetically acceptable vehicle for the azole and the lipid material.

2. The composition of claim 1 wherein the amount of the lipid material is from 0.0001 to 50 % by weight of the composition.

3. The composition of claim 1 wherein the weight ratio of the lipid material to the azole is in the range from about 1:100 to about 100:1.

4. The composition of claim 1 wherein the azole is selected from the group consisting of econazole, clotrimazole, bifonazole, miconazole, ketoconazole, butoconazole, climbazole, sulconazole, liarazole, and mixtures thereof.

5. A method of treating skin, hair, or nails which comprises applying topically thereto the composition of claim 1.

6. A method of improving or preventing the appearance of wrinkled, flaky, aged, photodamaged skin, the method comprising applying topically to skin the composition of claim 1.

* * * * *